US00PP19438P2

(12) United States Plant Patent
van Kleinwee

(10) Patent No.: US PP19,438 P2
(45) Date of Patent: Nov. 11, 2008

(54) *GERANIUM* PLANT 'ZOMON'

(50) Latin Name: *Pelargonium zonale (L) L'H'erit. ex Ait*
Varietal Denomination: Zomon

(75) Inventor: Theodorus Cornelis Maria van Kleinwee, Hoorn (NL)

(73) Assignee: Syngenta Seeds B.V., Enkhuizen (NL)

( * ) Notice: Subject to any disclaimer, the term of this patent is extended or adjusted under 35 U.S.C. 154(b) by 0 days.

(21) Appl. No.: 11/973,705

(22) Filed: Oct. 10, 2007

(51) Int. Cl.
*A01H 5/00* (2006.01)

(52) U.S. Cl. ..... Plt./330

(58) Field of Classification Search ..... Plt./330
See application file for complete search history.

(56) References Cited

PUBLICATIONS

UPOV–ROM search for PBR 20061304 for cultivar Zomon. P. 1.*

* cited by examiner

*Primary Examiner*—Annette H Para
(74) *Attorney, Agent, or Firm*—S. Matthew Edwards

(57) ABSTRACT

A new *Geranium* plant, particularly distinguished by its rather small, semi-double salmon flowers, rather compact plant habit, excellent branching, and dark green foliage with hardly any zoning.

1 Drawing Sheet

Latin name of the genus and species of the plant claimed: *Pelargonium zonale* (*L.*) *L'Hérit. ex Ait.*
Varietal denomination: 'Zomon'.

BACKGROUND OF THE NEW PLANT

The present invention comprises a new *Geranium*, botanically known as *Pelargonium zonale* (*L.*) *L'Hérit. ex Ait,* and hereinafter referred to by the variety name 'Zomon.'

The new *Geranium* is a product of a planned breeding program. This new *Geranium* plant has rather small, semi-double salmon flowers, is rather compact, has excellent branching, and has dark green foliage with hardly any zoning.

This new *Geranium* plant originated from a hybridization in a controlled environment in Enkhuizen, Netherlands. The female parent is an unpatented *Pelargonium zonale* (*L.*) *L'Hérit. ex Ait* seedling identified as 'K2002-2' with deep salmon, semi-double flowers, a vigorous, good branching plant habit, and middle green foliage with rather strong zoning. 'K2002-2' has more vigor, lighter green foliage, and stronger zoning in the leaves compared to 'Zomon.' The male parent is an unpatented *Pelargonium zonale* (*L.*) *L'Hérit. ex Ait* seedling identified as 'T0087-1' a rather compact variety with dark foliage and deep salmon semi-double flowers. 'T0087-1' has smaller flowers, a less branching character, and more petaloids in the flower compared to 'Zomon.'

'Zomon' was selected as a single flowering plant within the progeny of the stated cross in 2003 in a controlled environment in Enkhuizen, Netherlands.

The first act of asexual reproduction of 'Zomon' was accomplished when vegetative cuttings were taken from the initial selection in the Fall of 2003 in a controlled environment in Enkhuizen, Netherlands.

Horticultural examination of plants grown from cuttings of the plant initiated in April of 2004 in Enkhuizen, Netherlands, and continuing thereafter, has demonstrated that the combination of characteristics as herein disclosed for 'Zomon' is firmly fixed and is retained through successive generations of asexual reproduction.

'Zomon' has not been observed under all possible environmental conditions. The phenotype may vary significantly with variations in environment such as temperature, light intensity and day length.

DESCRIPTION OF THE DRAWING

The accompanying photographic drawing shows typical flower and foliage characteristics of 'Zomon' with colors being as true as possible with an illustration of this type. The photographic drawing shows a flowering potted plant of the new variety.

BOTANICAL DESCRIPTION OF THE PLANT

The measurements were taken in Enkhuizen, Netherlands, in July 2006 on plants that were growing in the field. Culture of these plants started in mid February 2006 in the greenhouse. Plants were transferred to the field in mid May 2006. The plant history was taken on 26 week old plants.

The following observations, measurements, and comparisons describe plants grown outside in Enkhuizen, Netherlands. The following traits have been repeatedly observed and are determined to be basic characteristics of the new variety. The combination of these characteristics distinguishes this *Geranium* as a new and distinct variety.

Color references are primarily to the R.H.S. Colour Chart of The Royal Horticultural Society of London, edition 2001.

TABLE 1

DIFFERENCES BETWEEN THE NEW VARIETY 'ZOMON' AND A SIMILAR VARIETY

| | 'Zomon' | 'Fisorange' U.S. Plant Patent No. 12,485) |
|---|---|---|
| Flower color | 52A | 40B |
| Plant vigor | Compact | Medium |
| Leaf color | Dark green | Middle green |

The plant:

*Plant height.*—10–13 cm.
*Plant height* (*inflorescence included*).—17–19 cm.
*Plant width.*—20–23 cm.
*Plant shape.*—Round.

The foliage:

*Length.*—3–4 cm.
*Width.*—6–7 cm.
*Shape.*—Peltate.
*Base shape.*—Cordate.
*Base size.*—0.5–1 cm.
*Apex shape.*—Rounded with weak lobes.
*Apex size.*—2–3 cm.
*Color of upper surface.*—137A.
*Color of lower surface.*—147B.
*Color of zone.*—No zoning.
*Color of veins.*—146C.
*Margin.*—Sinuate to Bicrenate.
*Petioles length.*—5.5–7.0 cm.
*Diameter of petiole.*—2–3 mm.
*Leaves pubescence.*—Lower surface rather high density of pubescence, upper surface medium pubescence.
*Texture of leaves.*—Leathery.
*Veins.*—Palmate.

The stem:

*Length of internodes.*—25–35 mm.
*Color of stem.*—144B.
*Diameter.*—6–7 mm.

The inflorescence:

*Shape.*—Round outline.
*Diameter.*—8.5–9 cm.
*Umbel depth.*—5–6 cm.
*Length of peduncle.*—9–14 cm.
*Peduncle diameter.*—3–5 mm.
*Color of peduncle.*—144B, some spots 177A.
*Length of pedicel.*—20–29 mm.
*Color of pedicel.*—144C, some anthocyanin 180B.
*Number of flowers per inflorescence.*—35–45.

The corolla:

*Form.*—Semi-double flower.
*Shape.*—Round outline, upper petals about the same size as the lower petals, flat to cup shaped.
*Length of flower.*—3.9 cm.
*Width of flower.*—3.6 cm.
*Number of petals.*—6–7.
*Length of petals* (*upper/lower*).—Upper 22 mm. Lower 22 mm.
*Width of petals* (*upper/lower*).—Upper 19 mm. Lower 14 mm.
*Shape petals.*—Obovate, base acute, upper end is truncate to rounded, margin is entire.
*Color.*—Upper side of upper petals: 52A.
*Color.*—Upper side of lower petals: 52A.
*Color.*—Lower side of upper petals: 52D.
*Color.*—Lower side of lower petals: 52C.
*Number of petaloids.*—2–3.
*Color petaloids.*—52B.
*Fading color when flower starts aging.*—No.
*Duration of flowering.*—Continuous flowering throughout the Summer.

The bud (just before opening):

*Shape.*—Narrow elliptic.
*Shape base of bud.*—Truncate.
*Shape top of bud.*—Acuminate.
*Sepals hairiness.*—Very pubescent.
*Length.*—12–14 mm.
*Width.*—7–8 mm.
*Color.*—144B.
*Number of sepals.*—5.
*Color of sepals.*—144B.
*Length of sepals.*—8–9 mm.
*Width of sepals.*—3–4 mm.

Reproductive organs:

*Number of lobes of stigma.*—5.
*Color stigma.*—50A.
*Length of style.*—4 mm.
*Color of style.*—50B.
*Number of anthers.*—8–9.
*Length of anthers.*—9 mm.
*Shape of anthers.*—Ovate.
*Length filaments.*—8 mm.
*Color of filaments.*—155D, near anther 52B.
*Pollen present.*—Yes.
*Pollen color.*—33A.

Seed development: Seed development has not been observed to date.

Disease/pest resistance: No disease/pest resistance has been observed to date.

What is claimed is:

1. A new and distinct variety of *Geranium* plant named 'Zomon,' as substantially illustrated and described herein.

* * * * *

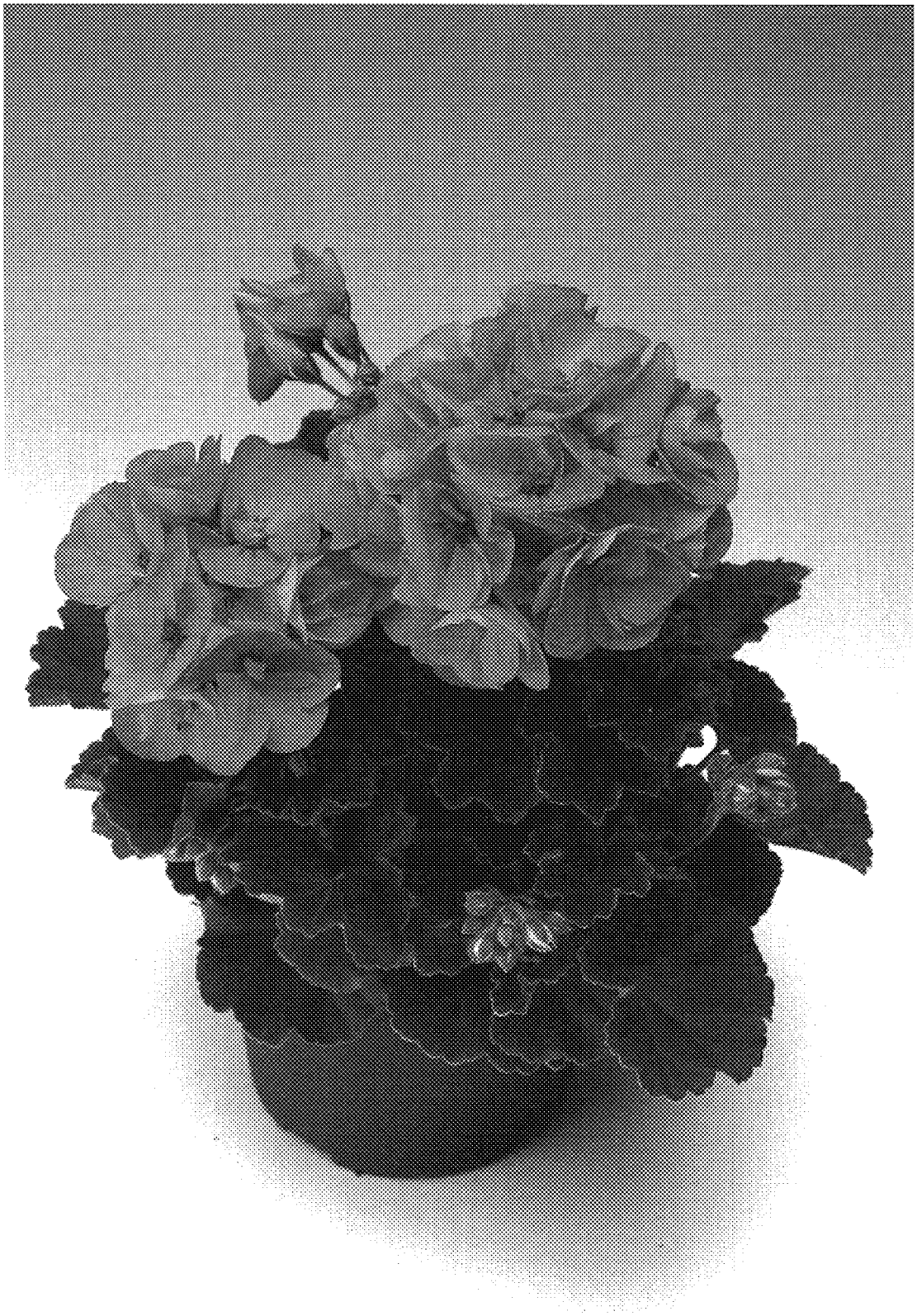

UNITED STATES PATENT AND TRADEMARK OFFICE

CERTIFICATE OF CORRECTION

PATENT NO. : PP 19,438 P2
APPLICATION NO. : 11/973705
DATED : November 11, 2008
INVENTOR(S) : van Kleinwee It is certified that error appears in the above-identified patent and that said Letters Patent is hereby corrected as shown below:

At column 1, at item (54), insert --NAMED-- following "PLANT"

At column 1, at item (50), delete "L'H'erit" and insert therefor --L'Hérit--

At column 3, at TABLE 1, insert --(-- before "U.S. Plant Patent No. 12,485)"

Signed and Sealed this

Thirtieth Day of December, 2008

JON W. DUDAS
*Director of the United States Patent and Trademark Office*